(12) United States Patent
Blancke et al.

(10) Patent No.: US 10,314,982 B2
(45) Date of Patent: Jun. 11, 2019

(54) DRUG DELIVERY DEVICE WITH ANTI-COUNTERFEIT FEATURES

(71) Applicant: Sanofi-Aventis Deutschland GmbH, Frankfurt am Main (DE)

(72) Inventors: Stefan Blancke, Frankfurt am Main (DE); Axel Teucher, Frankfurt am Main (DE); Michael Jugl, Frankfurt am Main (DE); Christiane Schneider, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 215 days.

(21) Appl. No.: 15/031,723

(22) PCT Filed: Nov. 17, 2014

(86) PCT No.: PCT/EP2014/074700
§ 371 (c)(1),
(2) Date: Apr. 23, 2016

(87) PCT Pub. No.: WO2015/074975
PCT Pub. Date: May 28, 2015

(65) Prior Publication Data
US 2016/0235927 A1 Aug. 18, 2016

Related U.S. Application Data

(60) Provisional application No. 61/907,476, filed on Nov. 22, 2013.

(30) Foreign Application Priority Data

Apr. 24, 2014 (EP) ..................................... 14165744

(51) Int. Cl.
*A61M 5/315* (2006.01)

(52) U.S. Cl.
CPC ...... *A61M 5/31576* (2013.01); *A61M 5/3155* (2013.01); *A61M 5/31533* (2013.01); *A61M 5/31545* (2013.01); *A61M 5/31565* (2013.01)

(58) Field of Classification Search
CPC .......... A61M 5/31576; A61M 5/31533; A61M 5/31545; A61M 5/3155; A61M 5/31565;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| EP | 0937471 A2 | 8/1999 |
| EP | 0937476 A2 | 8/1999 |

(Continued)

OTHER PUBLICATIONS

International Preliminary Report on Patentability and Written Opinion in Application No. PCT/EP2014/074700, dated May 24, 2016, 9 pages.

(Continued)

*Primary Examiner* — Kevin C Sirmons
*Assistant Examiner* — Leah J Swanson
(74) *Attorney, Agent, or Firm* — Fish & Richardson P.C.

(57) ABSTRACT

A drive assembly for a drug delivery device includes a housing; a number sleeve threadedly engaged with the housing; a dial link rotatably fixed with the number sleeve in a first axial arrangement relative to each other, the number sleeve being rotatable relative to the dial link in a second axial arrangement; a clutch component connected to an inner proximal section of the number sleeve through multiple flexible assembly fingers. The clutch component can engage the number sleeve with the dial link in the first axial (Continued)

arrangement and disengage the number sleeve from the dial link in the second axial arrangement. The drive assembly includes means for preventing an access to the flexible assembly fingers from the outer proximal section of the number sleeve and/or the flexible assembly fingers from flexing inwardly and disengaging from the connection with the inner proximal section.

16 Claims, 8 Drawing Sheets

(58) Field of Classification Search
CPC .......... A61M 5/31548; A61M 5/31551; A61M 5/31553; A61M 5/3156
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,291,132 B2 * | 11/2007 | DeRuntz ............ A61M 5/31551 604/187 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0129687 A1 * | 6/2007 | Marshall ................ A61M 5/20 604/207 |
| 2009/0275916 A1 | 11/2009 | Harms et al. | |

FOREIGN PATENT DOCUMENTS

| | | |
|---|---|---|
| JP | 2005-531348 | 10/2005 |
| JP | 2007-502146 | 2/2007 |
| JP | 2012-515029 | 7/2012 |
| WO | 9938554 A1 | 8/1999 |
| WO | 0110484 A1 | 2/2001 |
| WO | WO 2004/002556 | 1/2004 |
| WO | 2005018721 A1 | 3/2005 |
| WO | 2006126902 A1 | 11/2006 |
| WO | WO 2010/081854 | 7/2010 |
| WO | 2012049139 A1 | 4/2012 |
| WO | 2012049143 A1 | 4/2012 |

OTHER PUBLICATIONS

International Search Report in Application No. PCT/EP2014/074700, dated Mar. 3, 2015, 5 pages.

* cited by examiner

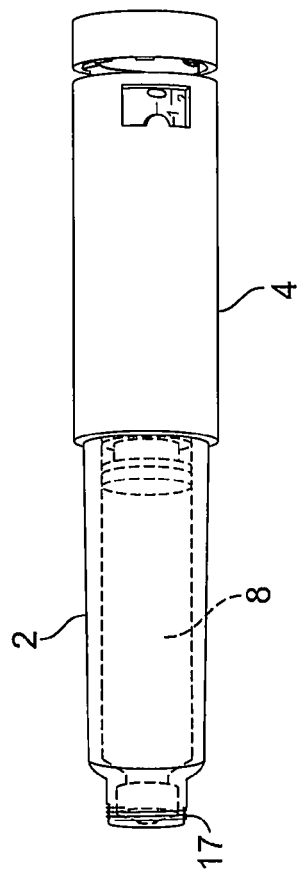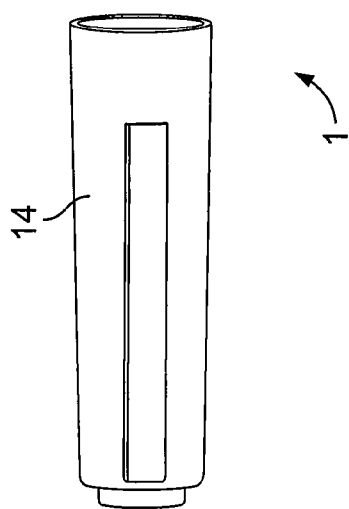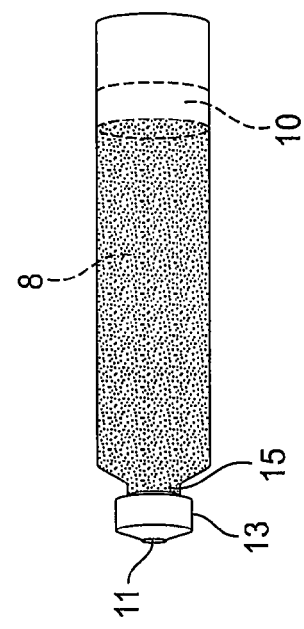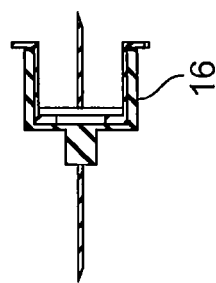

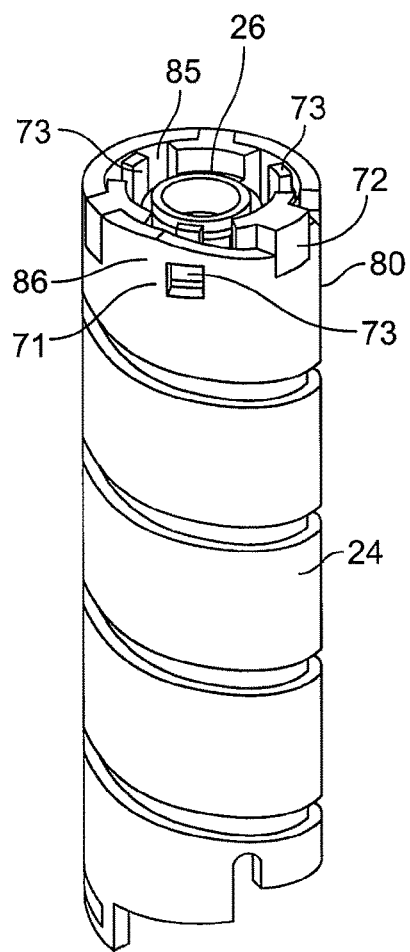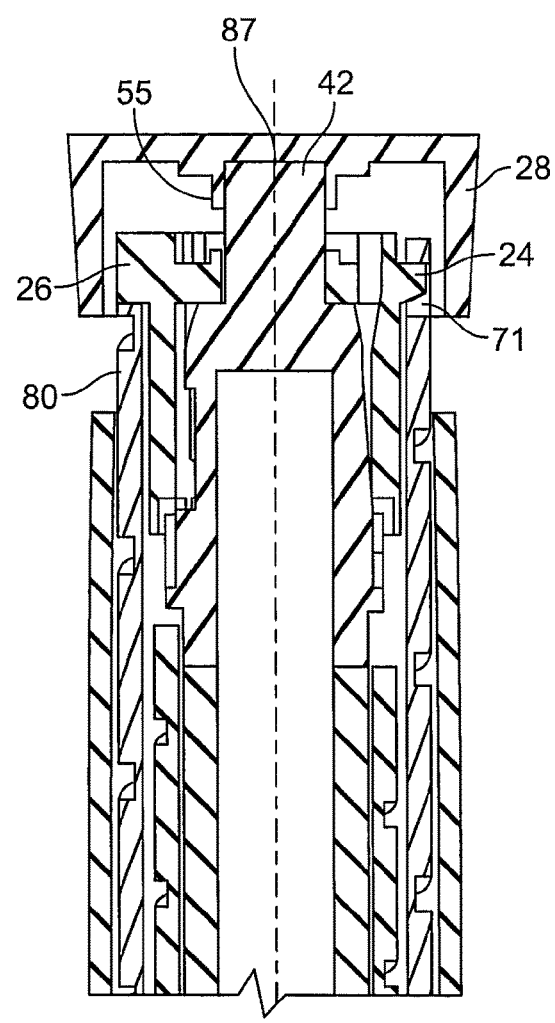
FIG. 4
FIG. 5

DRUG DELIVERY DEVICE WITH ANTI-COUNTERFEIT FEATURES

CROSS REFERENCE TO RELATED APPLICATIONS

The present application is a U.S. National Phase Application pursuant to 35 U.S.C. § 371 of International Application No. PCT/EP2014/074700 filed Nov. 17, 2014, which claims priority to U.S. Provisional Patent Application No. 61/907,476 filed Apr. 24, 2014. The entire disclosure contents of these applications are herewith incorporated by reference into the present application.

FIELD OF INVENTION

The present disclosure is generally directed to pen-type injection devices and specifically to a drive assembly for such drug delivery devices, providing a dose setting mechanism for setting a predetermined amount of a medicament. Such devices provide for self-administration of medicinal product from a multi-dose cartridge and permit a user to set the delivery dose. The present disclosure may find application in both disposable and reusable type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease. Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e., hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes and other disease states so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics, for instance, have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Generally, pen type injection devices include a cartridge having a slidable piston and containing a multi-dose quantity of liquid medication. A lead screw extending from the dose setting mechanism of the injector pen is movable in a forward (i.e., distal direction) to advance the piston within the cartridge in such a manner as to dispense the contained medication from an outlet at the opposite cartridge end, typically through a needle that penetrates a stopper or septum at that opposite end. In disposable or prefilled pens where the cartridge is permanently sealed within the pen housing, after a pen has been utilized to exhaust the supply of medication within the cartridge, the entire pen is then discarded. In reusable pens, after a pen has been utilized to exhaust the supply of medication within the cartridge, the pen is disassembled to allow replacement of the spent cartridge with a fresh cartridge, and then the pen is reassembled for its subsequent use.

A number of pen type injection devices are commercially available and unfortunately a number of those devices suffer from one or more design flaws that may result in the improper use of the injection device or the delivery of an inaccurate dosing of the medicament. Inaccurate dose setting could lead to fatal results. Other design flaws allow the possibility that a counterfeiter can dissemble a disposable pen and insert bogus medicament cartridge. This pen is then reassembled and sold as new. Such design flaws may not be realized when a pen is first commercialized and may only become apparent after the injection device has been in commercial use by patients for an extended period of time. As such, there exists a need to evaluate existing pen designs to identify the design flaws and then take corrective action, which typically would include redesigning certain original mechanisms within the injection device.

One such pen injector lending itself to design improvements is described in WO 2005/018721. The following describes a number of such design flaws and presents corrective solutions to eliminate these flaws.

SUMMARY

Most, if not all, pen injection type devices are designed to allow self-administration of medicament in preset doses by the patient suffering from one or more disease state. Depending on treatment regime set by the caregiver, a patient may have to perform injections several times a day. For this reason, pen type devices must be designed for all types of users (depending on the intended use of the device or the specific user group suffering from the disease which the device is made for), including the very young and the very old, who may suffer from poor vision or hearing or manual dexterity. Because most patients who self-administer injections are not as sophisticated as licensed caregivers, these users can be more easily taken advantage of by persons willing to engage in the selling of counterfeit injection devices. As such, it is imperative that newly designed injection devices should be carefully analyzed to determine if there are design flaws that would allow a counterfeiter to disassemble an otherwise sealed disposable pen type injection device in order to reset the dosing mechanism and to insert a bogus cartridge of medicament for illegal re-distribution to unsuspecting users.

A physical examination of the commercial pen injection device that is generally described in WO 2005/018721 or a pen injection device basing on a similar principle shows that a respective design provides a so called number sleeve and a clutch component coupling the number sleeve with at least another component, namely a dial link that itself may—at least temporarily—act together with other driving means of the device. The clutch component may act so as to engage the dial link with the number sleeve in a first operating state of the device and to disengage the dial link from the number sleeve in a second operating state of the device.

Such a design of the number sleeve and clutch connection often uses a number of holes, e.g. cut-out through holes that accept snap arms and respective flexible assembly fingers to retain these two parts together. The design may have the inconvenience that these holes are readily accessible by a user and can be manipulated with a small screwdriver or other such tool to disengage the snap arms and respective flexible assembly fingers to allow the dose knob and/or the clutch to be removed from the proximal end of the device. In the worst case, the device is then corrupt and cannot be used anymore. Moreover, the dose setting mechanism can then be removed from the housing and the lead screw reset to the initial pre-use position. A cartridge of bogus medicament could then be used to replace the spent cartridge and the pen device reassembled for re-use by an unsuspecting user.

To solve these problems, the present disclosure generally provides a drive assembly as well as a drug delivery device with such a drive assembly which overcome the aforementioned deficiencies.

The disclosed drive assembly and drug delivery device with such a drive assembly have the advantage that the clutch component can be simply provided with its respective functionality on the number sleeve without risking a disassembly and potential damage of the device.

The drive assembly provides means for fulfilling a double prevention. On the one hand, an access to the plurality of flexible assembly fingers from the outer proximal section of the number sleeve is prevented. This means that a user cannot manipulate the device, especially the clutch component on the number sleeve, with a tool, e.g. a screwdriver, from the outer proximal section of the number sleeve, that means from the outside. On the other hand, the plurality of flexible assembly fingers is prevented from flexing inwardly and disengaging from the connection with the inner proximal section of the number sleeve. Besides a general prevention of an access to the flexible assembly fingers from the outer proximal section, the second prevention function secures a stable connection between the clutch component and the number sleeve as the flexible assembly fingers cannot be maneuvered anymore, once they are in connection with the inner proximal section of the number sleeve.

According to the drive assembly of claim 1, the clutch component and the number sleeve can be fabricated as separate parts and then be assembled together for fulfilling their duties. The prevention means, however, guarantee a stable functionality of the drive assembly, since a manipulation on the coupling between the separate parts, i.e. on both the flexible assembly fingers or the inner proximal section of the number sleeve, is prevented.

The drive assembly provides a number sleeve and clutch component, wherein the clutch component is an integral part of the inner proximal section of the number sleeve. According to such an embodiment, the number sleeve is fabricated as an integral part forming a respective clutch component for fulfilling a respective engagement and disengagement of the number sleeve with and from the dial link. Such an integral fabrication of the number sleeve has the advantage that neither flexible assembly fingers nor respective counter detent means are necessary.

Further herein, a method and system for providing a drug delivery device are provided. The device comprises a drug delivery device housing and a medicament contained in the drug delivery device housing where anti-counterfeiting solutions include components to prevent the assembly fingers from flexing inward and disengaging from the number sleeve. Elimination of the assembly fingers by integrating the clutch with the number sleeve is also presented as well as the use of detent pockets in place of cut-out through holes.

Moreover, some embodiments are presented that modify the original design of the injection device described in the WO 2005/018721 publication in particular to provide several alternatives that will prevent disassembly of the device. One solution to the problem involves not using a cut-out or window in the proximal end of the number sleeve to capture the assembly fingers of the clutch component. Instead, indentations or detents are used on the inside proximal circumference of the number sleeve to accept the assembly fingers. According to a second alternative, a ring is used inside the proximal end of the number sleeve to block or prevent the assembly fingers or snap arms on the clutch from flexing inward and disengaging from the cut-outs. Alternatively, the ring could be positioned on the outside of the number sleeve to cover or block access to the cut-outs. This ring could be a separate stand-alone part or it could be incorporated into a redesign of the dose knob. Yet another solution to the problem involves eliminating the need for a separate number sleeve and a separate clutch and to combine both parts into a single part, thus eliminating the possibility that the clutch assembly fingers could be de-latched from the number sleeve as in the current commercial design.

The pen type drug delivery device including the above described design improvement includes a housing, a lead screw having a threaded shaft is rotatably fixed during dose setting and injecting that only moves axially in a distal direction relative to the housing during dose administration and is always prevented from moving proximally. The device also has a fluid container or cartridge defining a medicine-filled reservoir with a movable piston at one end and an outlet at the other end, where the piston is engaged by a bearing connected to the distal end of the lead screw. The piston is advanced toward the outlet or distal end of the cartridge when the lead screw is moved distally during dose administration.

A drive nut is threadedly engaged with the threads on the lead screw and can rotate and move proximally relative to the lead screw and housing during dose setting. A number sleeve is threadedly engaged with the housing and is screwed outwardly in the proximal direction relative to the housing during dose setting. A dial link is slidably and rotationally engaged with the drive nut and is axially movable and rotatably fixed relative to the drive nut. The dial link is rotatably fixed with the number sleeve through a clutch when the dial link and number sleeve are in a first axial arrangement and when in a second axial position the clutch, and hence the number sleeve, are disengaged from the dial link and the dial link becomes rotatable relative to the number sleeve. An inner sleeve is threadedly engaged with the number sleeve, were the inner sleeve is axially movable but rotatably fixed relative to the housing. During dose setting, the dial link and the number sleeve are in the first axial arrangement, whereby a screwing motion of the dose knob that is connected to the dial link and number sleeve relative to the housing screws the dial link and the number sleeve a first axial distance from a home position causing the number sleeve to extend in the proximal direction outwardly from the housing or body of the device. The screwing motion of the dial link screws the drive nut along the lead screw threaded shaft a second axial distance different than the first axial distance.

During dose dispensing, the dial link and the number sleeve element are in the second axial arrangement, whereby a screwing motion of the number sleeve relative to the housing back or inward toward the home position advances the inner sleeve without rotation in the distal direction to axially advance the drive nut and thereby the lead screw and the fluid container piston to dispense medicine from the outlet. The pen injector disclosed herein can be provided with a mechanical advantage that makes it easier for the user to push the dose knob during the dispensing of medication, which mechanical advantage can be very high and conveniently selected by the manufacturer during apparatus design. This mechanical advantage allows the number sleeve to travel a greater axial distance than the lead screw it advances, thus allowing for small doses to be delivered.

In the following an enumeration of advantageous aspects and embodiments of a device as presented herein is given:

1. A drug delivery device comprising:
a housing;
a lead screw having a distal end and a proximal end that is rotatably fixed during dose setting and dose delivery and axially movable in a distal direction relative to the housing, the lead screw including a threaded shaft and a bearing foot connected to the distal end;
a cartridge with a movable piston at one end and an outlet at the other end, the piston engagable by the lead screw bearing foot to be advanced toward said outlet when the lead screw is moved distally;
a drive nut threadedly engaged and screwable along the lead screw threaded shaft;
a number sleeve threadedly engaged with the housing to be screwable relative to the housing, where the number sleeve has inner and outer proximal sections;
a dial link connected with the drive nut and axially movable and rotatably fixed relative to the drive nut, the dial link rotatably fixed with the number sleeve when the dial link and number sleeve are in a first axial arrangement, the number sleeve is rotatable relative to the dial link when the dial link and number sleeve are in a second axial arrangement;
a clutch component configured to engage the dial link during dose setting and that is connected to the inner proximal section of the number sleeve through a plurality of flexible assembly fingers, where the assembly fingers are not accessible from the outer proximal section of the number sleeve;
an inner sleeve threadedly engaged with the number sleeve, the inner sleeve axially movable and rotatably fixed relative to the housing;
a mid-body axially fixed inside of the housing, the mid-body including tabs that slidably fit within keyways in the lead screw to prevent rotation of the lead screw within the housing, wherein the inner sleeve is axially movable and rotatably fixed relative to the mid-body by at least one lug of the mid-body that slidably fits within at least one slot formed in the inner sleeve; and
wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;
wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws the drive nut along the lead screw threaded shaft a second axial distance that is different than the first axial distance; and
wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

2. The drug delivery device as explained in number 1 where the assembly fingers are in a snap fit engagement with detent pockets on the inner proximal section of the number sleeve.

3. A drug delivery device comprising:
a housing;
a lead screw having a distal end and a proximal end that is rotatably fixed during dose setting and dose delivery and axially movable in a distal direction relative to the housing, the lead screw including a threaded shaft and a bearing foot connected to the distal end;
a cartridge with a movable piston at one end and an outlet at the other end, the piston engagable by the lead screw bearing to be advanced toward said outlet when the lead screw is moved distally;
a drive nut threadedly engaged and screwable along the lead screw threaded shaft;
a number sleeve threadedly engaged with the housing to be screwable relative to the housing, where the number sleeve has inner and outer proximal sections and the outer proximal section does not contain cut-out through holes;
a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement;
a clutch component configured to engage the dial link during dose setting and that is an integral part of the inner proximal of the number sleeve and does not have a plurality of flexible assembly fingers;
an inner sleeve threadedly engaged with the number sleeve, the inner sleeve is axially movable and rotatably fixed relative to the housing;
a mid-body axially fixed inside of the housing, the mid-body including tabs that slidably fit within keyways in the lead screw to prevent rotation of the lead screw within the housing, wherein the inner sleeve is axially movable and rotatably fixed relative to the mid-body by at least one lug of the mid-body that slidably fits within at least one slot formed in the inner sleeve; and
wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;
wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threaded shaft a second axial distance that is different than the first axial distance; and wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

4. A drug delivery device comprising:
a housing;
a lead screw having a distal end and a proximal end that is rotatably fixed during dose setting and dose delivery and axially movable in a distal direction relative to the housing, the lead screw including a threaded shaft and a bearing foot connected to the distal end;
a cartridge with a movable piston at one end and an outlet at the other end, the piston engagable by the lead screw bearing foot to be advanced toward said outlet when the lead screw is moved distally;
a drive nut threadedly engaged and screwable along the lead screw threaded shaft;
a number sleeve threadedly engaged with the housing to be screwable relative to the housing, where the number sleeve has inner and outer proximal sections;
a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement;
a clutch component configured to engage the dial link during dose setting and that is connected to the inner proximal section of the number sleeve through a plurality of flexible assembly fingers engaged with cut-out through holes in the outer proximal section of the number sleeve, where a ring is positioned in an annular space between the dial link and assembly fingers such that the ring prevents the assembly fingers from flexing inwardly and disengaging from the cut-out through holes;
an inner sleeve threadedly engaged with the number sleeve, the inner sleeve axially movable and rotatably fixed relative to the housing;
a mid-body axially fixed inside of the housing, the mid-body including tabs that slidably fit within keyways in the lead screw to prevent rotation of the lead screw within the housing, wherein the inner sleeve is axially movable and rotatably fixed relative to the mid-body by at least one lug of the mid-body that slidably fits within at least one slot formed in the inner sleeve; and
wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;
wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threaded shaft a second axial distance that is different than the first axial distance; and wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

5. The drug delivery device as explained in number 4 where the ring is an integral part of a dose knob connected to the dial link.

6. A drug delivery device comprising:
a housing;
a lead screw having a distal end and a proximal end that is rotatably fixed during dose setting and dose delivery and axially movable in a distal direction relative to the housing, the lead screw including a threaded shaft and a bearing foot connected to the distal end;
a cartridge with a movable piston at one end and an outlet at the other end, the piston engagable by the lead screw bearing foot to be advanced toward said outlet when the lead screw is moved distally;
a drive nut threadedly engaged and screwable along the lead screw threaded shaft;
a number sleeve threadedly engaged with the housing to be screwable relative to the housing, where the number sleeve has inner and outer proximal sections;
a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement;
a clutch component configured to engage the dial link during dose setting and that is connected to the inner proximal section of the number sleeve through a plurality of flexible assembly fingers engaged with cut-out through holes in the outer proximal section of the number sleeve, where a ring is positioned around the outer proximal section of the number sleeve to block access to the assembly fingers;
an inner sleeve threadedly engaged with the number sleeve, the inner sleeve axially movable and rotatably fixed relative to the housing;
a mid-body axially fixed inside of the housing, the mid-body including tabs that slidably fit within keyways in the lead screw to prevent rotation of the lead screw within the housing, wherein the inner sleeve is axially movable and rotatably fixed relative to the mid-body by at least one lug of the mid-body that slidably fits within at least one slot formed in the inner sleeve; and
wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;
wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threaded shaft a second axial distance that is different than the first axial distance; and wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

These as well as other advantages of the various aspects of our improved drug delivery device, and the manner of attaining them, will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 is an illustration of one embodiment of the present invention showing the assembled pen type medication dispensing apparatus where the cap has been removed to reveal the cartridge container affixed to the dose setting mechanism;

FIG. 2 is a close up view of the cartridge container and the pen needle that is attached to the cartridge container for injection of the medicament;

FIG. 4 is a perspective view of the number sleeve and clutch interaction of a device;

FIG. 5 is a cross-sectional view of the number sleeve and clutch interaction from FIG. 4;

Figure 3:
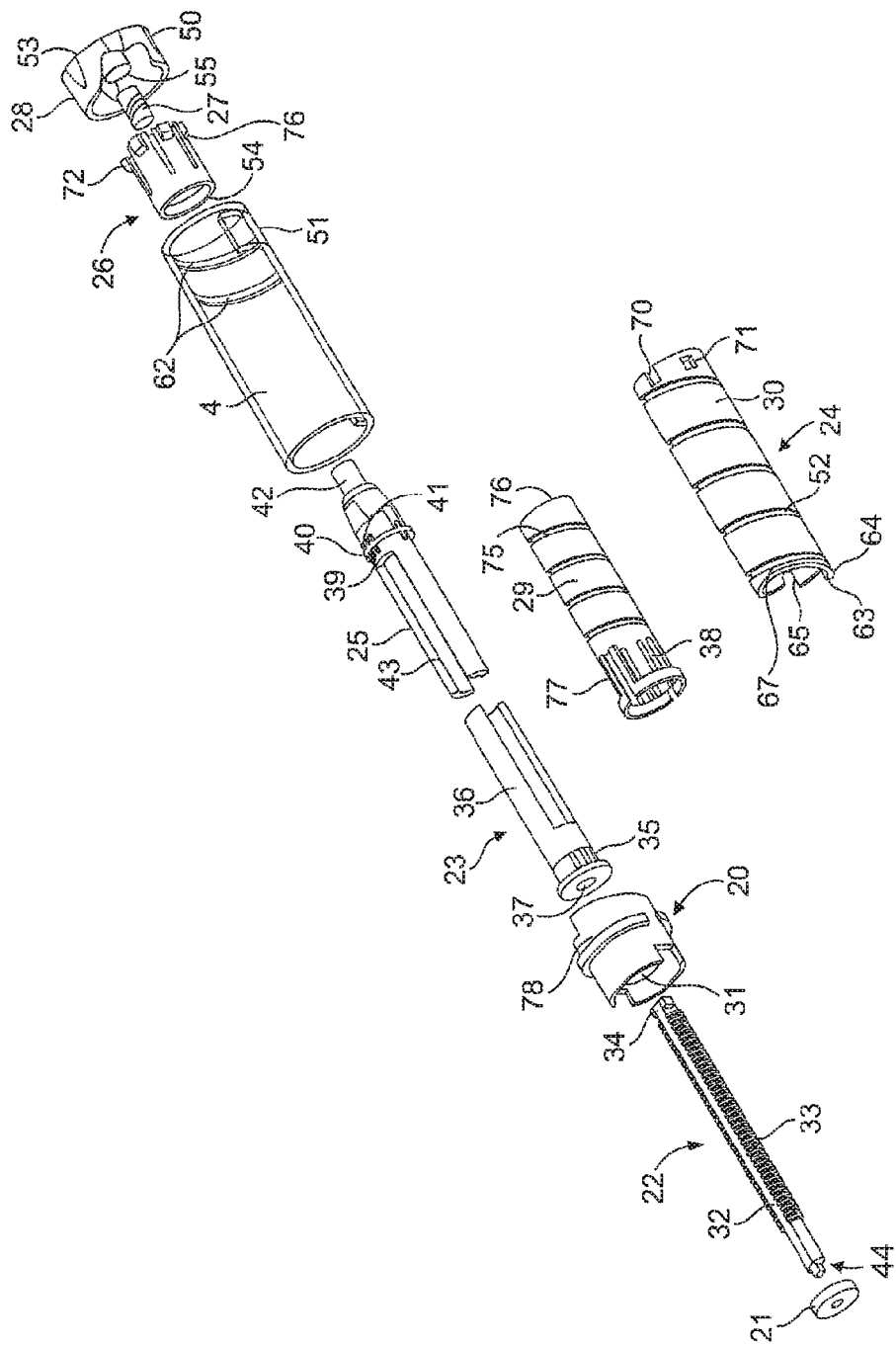
FIG. 3 is an exploded view of the embodiment from FIG. 1 showing each of the individual parts arranged relative to each other as they exist in the fully assembled device.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Referring first to FIGS. 1 to 3, there is shown a drug delivery device 1 as an injector pen, which pen has an elongated, substantially writing instrument-like form, although other forms are within the scope of the invention. In other words, the drug delivery device 1 may be a pen-type device. The drug delivery device 1 comprises a housing having a cartridge holder 2, and a main (exterior) body or housing 4.

The drug delivery device 1 and the housing have a distal end and a proximal end. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis or rotational axis of the device 1.

The proximal end of the cartridge holder 2 and the distal end of the main housing 4 are secured together by appropriate retaining features depending on whether the pen injector is designed as a reusable device or as a disposable device. In the latter case, the retaining feature would be permanent using the connection means described below. If the device is reusable, the retaining meaning would be a screw-type connection, a Luerlok, snap fit, bayonet, or the like type or combination of fittings that allow the user to easily disassemble the device to replace the empty cartridge with a fresh new cartridge. In this illustrated arrangement, the cartridge holder 2 is secured within the proximal end of the main body 4.

A cartridge 8 from which a number of doses of a medicinal product may be dispensed is provided in the cartridge holder 2. Preferably, the cartridge 8 contains a type of medicament that must be administered often, such as once or more times a day. One such medicament is insulin. A piston 10 shown in FIG. 2 is initially retained in the proximal end of the cartridge 8 and as each injection is completed gradually moves distally to the empty cartridge position. A removable cap 14 is releasably retained connected to the main body 4 covering the cartridge holder 2.

The dose setting mechanism of the drug delivery device illustrated in FIGS. 1 to 3 may be utilized as either for a disposable or reusable drug delivery device. Where the drug delivery device 1 comprises a disposable drug delivery device, the cartridge 8 cannot be removed from the device 1 without destroying the device 1. In a disposable device, the proximal end of the cartridge holder 2 can be fixedly mounted or secured, via adhesives, ultrasonic welding or in another suitable manner, to the dose setting mechanism housing when the injector pen is assembled by the manufacturer. Alternatively, where the drug delivery device 1 comprises a reusable drug delivery device, the cartridge 8 is removable and may be removed from the device 1 without destroying the device 1. In the drug delivery device 1 illustrated in FIGS. 1-3, the device 1 is illustrated as a disposable drug delivery device. However, those of ordinary skill in the art will recognize that the dose setting mechanism could also be used on reusable drug delivery devices as well, while in the case of a reusable pen, wherein the cartridge holder 2 may be reusable, such that the proximal end can be removably mounted or secured, for example via a threaded, bayonet, or snap fit connection, to a reusable dose setting mechanism having a resettable lead screw.

The previously mentioned removable or replaceable cap 14 is used to cover the cartridge holder 2 extending from the main housing 4. Preferably, the outer dimensions of the replaceable cap 14 are similar to or identical to the outer dimensions of the main housing 4 so as to provide an impression of a unitary whole part when the replaceable cap 14 is in position covering the cartridge holder 2. In use, the removable cap 14 is removed and a pen needle assembly 16 comprising a double-ended needle mounted in a hub may be screwed or pushed onto the distal end 17 of the cartridge holder 2 or, alternatively, may be snapped onto this distal end.

Cartridge 8 is of conventional design and defines a medicine-filled reservoir that is closed at its proximal end by the piston 10 that is axially slidably and sealably engaged with the cartridge interior wall to hold the fluid medication within the reservoir. The distal, outlet end of the cartridge reservoir is sealed by a septum 11 held by a cap 13 that is secured to a stepped-down diameter neck portion 15 of the cartridge 8. When the pen needle assembly 16 is mounted on the distal end of the cartridge holder 2, the proximal point of the injection needle passes through a central opening in the distal end of the cartridge holder 2, an opening in the cap 13, and penetrates the cartridge septum 11 to provide a fluid flow outlet by which medicine within the cartridge reservoir can be dispensed from the distal needle tip during operations of injector pen 1. The fluid medicine cartridge 8 shown and described above is illustrative and not intended to be limiting as other constructions may be employed within the scope of this invention.

Main body 4 of injector pen 1 houses an axially advanceable lead screw 22, a drive nut 23, an inner sleeve 29, a dial link 25, a number sleeve 24, a clutch 26, and a compression spring 27. A dose knob 28 is connected to the dial link 25 and is used to set the dose and then to inject the set dose. Housing or main body 4 is formed from a lightweight material, such as injection molded plastic. The housing 4 may be molded as a single, tubular piece for robustness. A window 51 in the housing 4 near its proximal end can be filled with a magnifying lens that snap-fits to the housing 4 and allows dosage indicating markings (not shown) on number sleeve 24 to be readily visible during use.

Near the interior distal end of the housing 4 is mounted a mid-body 20 that is formed with a central opening having an inward facing anti-rotation mechanism formed from a pair of diametrically opposed elements or tabs 31 having squared off inward ends that each slidably fit within longitudinal keyways 32 in the lead screw 22. In alternate embodiments, features other than tabs and keyways, for instance a lead screw with flats that fits within a complementarily shaped hole in a collar, may be used to prevent rotation. The tabs 31 prevent the lead screw 22 from rotating within the housing 4 during pen use, but permit the lead screw 22 to be shifted longitudinally, such as in the distal direction towards the cartridge 8. A snap fit or sonic welding connection of the mid-body 20 to the tubular housing 4 can be used to prevent axial and rotational relative motion of the mid-body 20 to the housing 4.

The lead screw 22 is in the form of a screw that is axially translatable and rotatably fixed during dosing and injecting. The term "rotatably fixed" shall mean in this context that the lead screw 22 is prevented from rotation during dosing and injecting. The lead screw 22 includes a shaft with a helical threading 33 along its length, which threading 33 is interrupted by the longitudinally extending keyways or grooves 32. A thread stop 34 shown at the proximal end of the threading 33 is provided and is used in preventing the pen from being set by a user to deliver a dose of medicine larger than remains in cartridge 8. Other forms of stopping the screw motion may be substituted within the scope of the invention, for example, the threading at the proximal screw end could stop near the proximal end where it can not be cammed in, and such solid screw with thread stop better ensures the nut 23 will not be torqued off the screw during dose setting. The distal end of lead screw 22 includes an enlarged, disc-shaped foot or bearing 21 to distribute loading on the cartridge piston 10 that the bearing 21 contacts and thereby directly engages during the piston 10 advancing. The separate bearing foot 21 can be attached, such as with a snap fit 44 that may permit relative rotation, to the lead screw 22. The lead screw 22 is shown as being a one-piece plastic injection molding, but alternate materials of construction and multiple pieces are possible.

The drive nut 23 includes a cylindrical, tube-shaped body with flexible fingers 36 and clicker teeth 35. The distal region of the drive nut 23 is formed with an internal threading 37 that threadedly engages in a friction locking fashion the threading 33 on the lead screw 22. Threadings 33 and 37 are shown as a double start threading but may be differently formed while still providing suitable friction locking capabilities, such as a single start threading or another multiple start threading. The drive nut 23 is located within the inner sleeve 29 and is axially, but not rotationally fixed, to the inner sleeve 29. As the drive nut 23 is rotated relative to inner sleeve 29 during dose setting, the clicker teeth 35 engage in a ratchet fashion flexible arms 38 that project radially on the inside of the inner sleeve 29. As the drive nut 23 rotates, the flexible arms 38 ride over the teeth 35 creating an audible clicking noise. The teeth 35 are configured so that each click is equal to one dose volume being set. As few as one flexible clicker arm 38 may be provided, but the use of four equally angularly spaced arms 38 aids in centering the drive nut 23 within the inner sleeve 29. The hollow interior of the drive nut body 23 located proximally of the threading 37 allows free passage of the proximal end of the lead screw 22. The exterior surface of the drive nut 23 is designed to cooperatively engage with the dial link 25 so that the dial link 25 is axially free and rotatably fixed relative to the drive nut 23. Thus, during use the dial link 25 is axially moveable relative to, but rotatably locked with, the threaded drive nut 23. This connection is possible because of the cooperation of the proximally extending fingers 36 on the drive nut 23 and the distally extending fingers 43 of the dial link 25. These two sets of fingers 36, 43 move axially relative to each other but engage each other rotationally during dose setting when the dial link 25 is rotated by turning the dose knob 28, which is fixed to the dial link 25. The drive nut 23 is shown as being a one-piece plastic injection molding, but other constructions are within the scope of the invention.

In the shown embodiment, the dial link 25 is formed in one piece of an injection molded plastic and which fits within the body 4. A flange 40 that rings a central region of the dial link body includes splines or teeth 39 that extend from the distal face of the flange 40, and teeth 41 that extend from the proximal face of the flange 40. A stepped-down portion of the proximal end of the dial link 25 forms an axially and proximally extending stem 42. The distal end of the dial link body includes the pair of fingers 43 that fit with the fingers 36 of the drive nut 23 to allow axial motion but not rotational motion of the drive nut 23 relative to the dial link 25, thereby rotationally locking the pieces together within the same annular space. Fingers 36 and 43 extend sufficiently axially to ensure they do not disengage during the setting of the maximum pen dose for injection.

An injection molded plastic dose knob 28 with a proximal face, and having a distally facing and centrally located bearing collar and alignment post is provided. The stem 42 of the of the dial link 25 receives the dose knob alignment post and can be ultrasonically welded within the bearing collar during manufacturing assembly, so as to axially and rotatably fix together the dose knob 28 and the dial link 25. The term "rotatably fix" shall mean in this context that any relative rotational movement between the dose knob 28 and the dial link 25 is prevented. A dose knob skirt 50 distally extends from the radial periphery of the dose knob distal face to serve as a grip portion for a user during dose setting. Coaxially mounted around the dial link 25 is the number sleeve 24. The number sleeve 24 has a cylindrical exterior surface 30 with a threading 52 formed as a helical groove that engages a corresponding threading 62 formed on the interior surface of body 4 to threadedly engage the number sleeve 24 to the pen housing. Threadings 52 and 62 are shown as a single start threading but may be differently formed. Threading 62 abuts an end 63 of threading 52 on the number sleeve 24 at the maximum pen dose, assuming the cartridge 8 is sufficiently full for such a maximum dose. A stop surface 64 on the distal end of the outer surface of the number sleeve 24 is positioned in slightly spaced apart relationship with a projecting stop at the zero dose position, and another stop surface is to be abutted by the stop if a user attempts to manually screw the screw element below a zero dose position. A hollow interior 65 of the number sleeve 24 is defined by a cylindrical interior surface provided with a helical threading 67. A ring of axially extending teeth 54 on the clutch 26 formed in the interior surface of flange cooperate with the dial link teeth 41 proximally facing on the dial link 25. The number sleeve 24 includes around its exterior surface 30 suitable indicia (not shown) of therapeutic dose size as visible through the opening 51 of the body 4.

The outside diameter of the number sleeve 24 is selected such that it can fit inside the dose knob 28. The proximal end region 80 of the number sleeve 24 includes an inner section 85 and an outer section 86 as illustrated in FIG. 4. The proximal end region 80 also contains a number of notches 70 and corresponding windows or cut-out through holes 71 that are alternately spaced around the circumference. In one embodiment a separate clutch 26 fits within the open proximal end of the number sleeve 24. As shown in FIGS. 4 and 5 ears 72 on the clutch 26 fit within notches 70 and flexible assembly fingers 73 by a snap-lock into cut-out through holes 71 to axially and rotatably lock the number sleeve 24 and the clutch 26 together during manufacturing assembly. The dose knob 28 is positioned on the stem 42 using an alignment post 55 and then is connected to the dial link stem 42 through an ultrasonic weld 87. After assembly it is possible to disengage the assembly fingers 73 from cut-out through holes 71 using a small pointed tool to flex the assembly fingers 73 inwardly such that they no longer engage the cut-out through holes 71 as illustrated in FIGS. 4 and 5. Once the assembly fingers 73 are flexed inward, the dose knob 28 and attached dial link 25 and clutch 26 can be removed from the inner proximal section 85 of the number sleeve 24. Once this occurs it is possible to further disassemble the device such that a counterfeiter could reset the dose setting mechanism and replace the spent empty cartridge 8 with a bogus cartridge of medicament.

Figure 6:
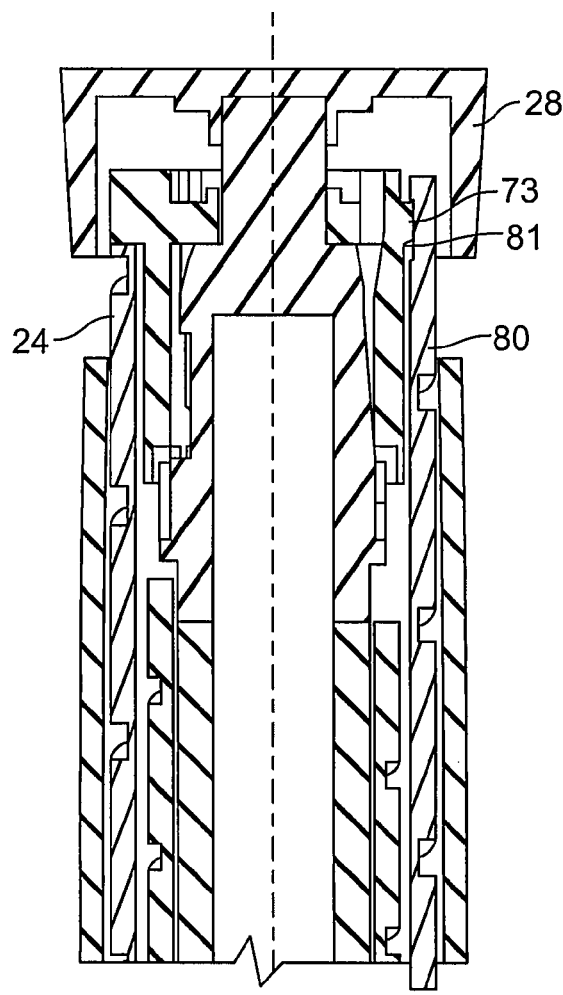
FIG. 6 is a cross-sectional view of one embodiment of a drive assembly where the cut-outs are replaced by detents or pockets.

FIG. 6 presents one design that prevents the assembly fingers 73 from being disengaged from the number sleeve 24. In this embodiment, the cut-out through holes 71 are replaced with detent pockets 81 that are located only on the inner proximal section 85 of the number sleeve 24. Because the detent pockets 81 are not accessible from the outer proximal section 86 of the number sleeve 24, the assembly fingers 73 cannot be flexed inwardly and disengaged from the detent pockets 81.

Figure 7:
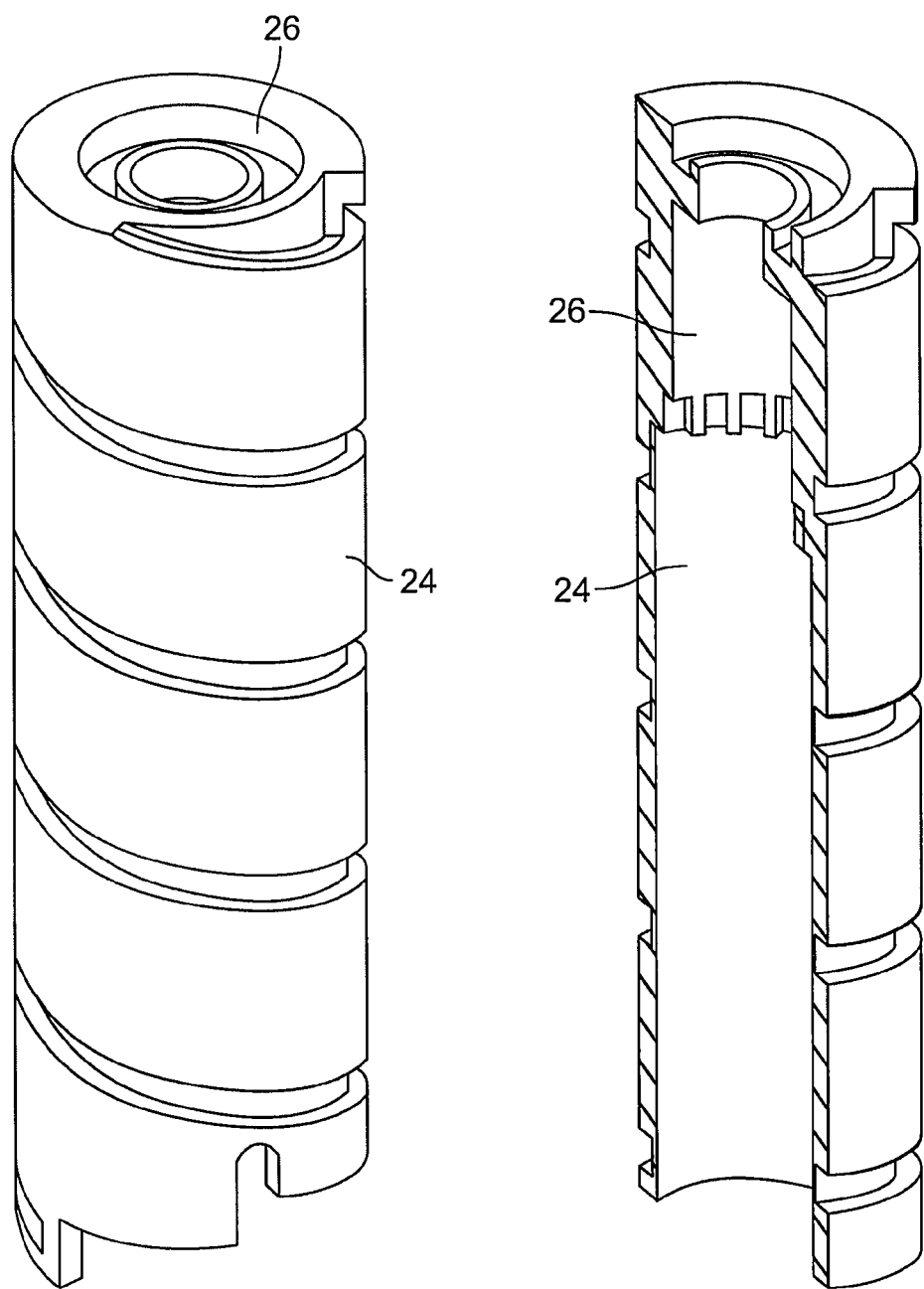
FIG. 7 is a perspective view and a cut-away view of a second embodiment of a drive assembly where the cut-outs in the number sleeve are eliminated and the clutch and number sleeve are a single part.

FIG. 7 illustrates a second solution to preventing disassembly. Here the clutch 26 and the number sleeve 24 are formed or manufactured as a unitary part. In other words, the clutch 26 is integral to the proximal portion of the number sleeve 24. This design eliminates the presence or need for assembly fingers 73 and cut-out through holes 71 in the number sleeve 24.

Figure 8:
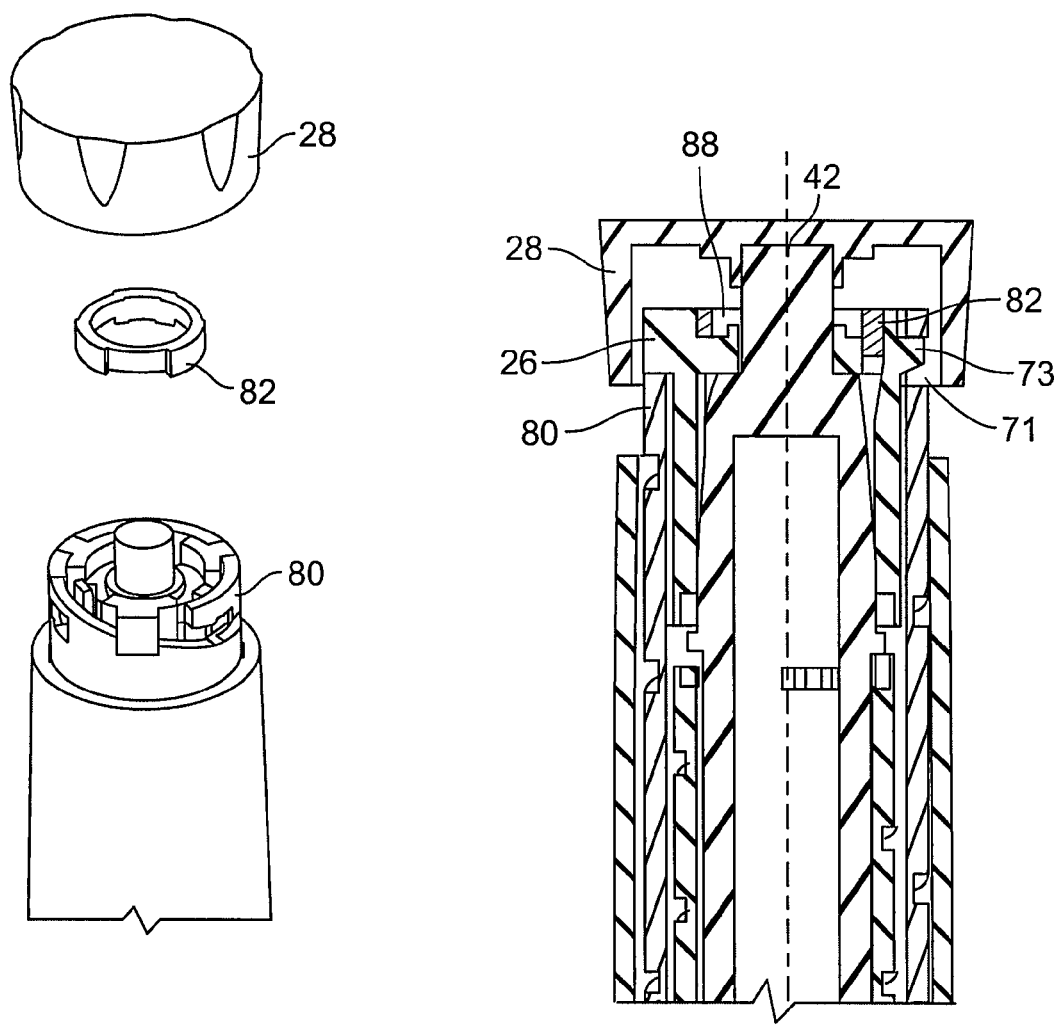
FIG. 8 is a perspective view and a cross-sectional view of a third embodiment of a drive assembly where an inner ring is placed inside the proximal end of the number sleeve to prevent movement of the clutch assembly fingers.

FIG. 8 presents a third possible solution that uses an inner ring 82 that is positioned in an annular space 88 between the dial link stem 42 and the inner proximal section 85. This inner ring 82 can be placed in the annular space 88 during assembly after the clutch 26 is snapped into place through the assembly fingers 73 engaging the cut-out through holes 71. Once in place, the ring 82 will be positioned on the inner side of the assembly fingers 73 and will prevent the assembly fingers 73 from flexing inwardly and disengaging from the cut-out through holes 71. Instead of a ring 82—formed by one piece—at least one ring segment can be provided.

Figure 9:
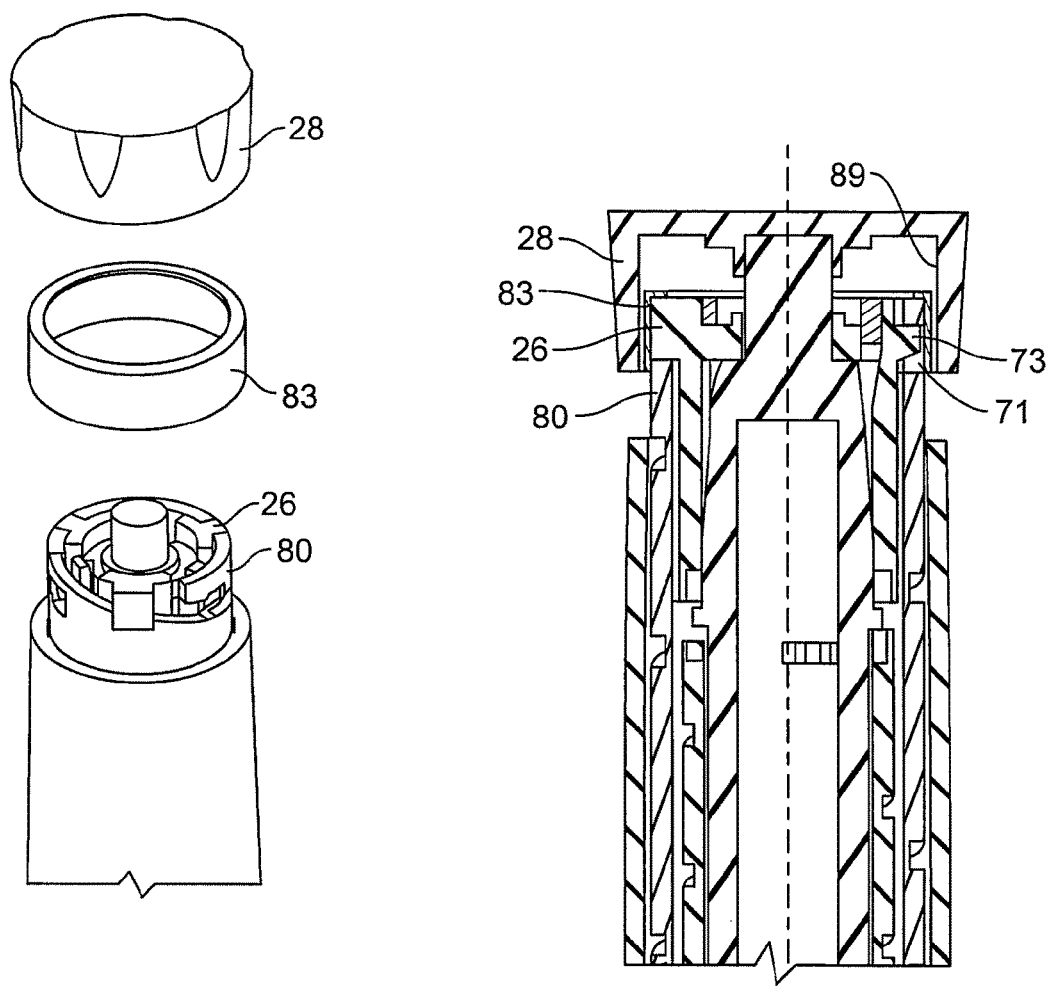
FIG. 9 is a perspective view and a cross-sectional view of a fourth embodiment of a drive assembly where an outer ring is placed over the proximal end of the number sleeve to prevent movement of the clutch assembly fingers.

A variation of this third solution is presented in FIG. 9, where instead of an inner ring 82 an outer ring 83 is used and placed between the number sleeve 24 and an inner skirt surface 89 of the dose knob 28. The outer ring 83 will cover or block an access to the cut-out through holes 71 and thus prevents an inwardly flexing of the assembly fingers 73.

Figure 10:
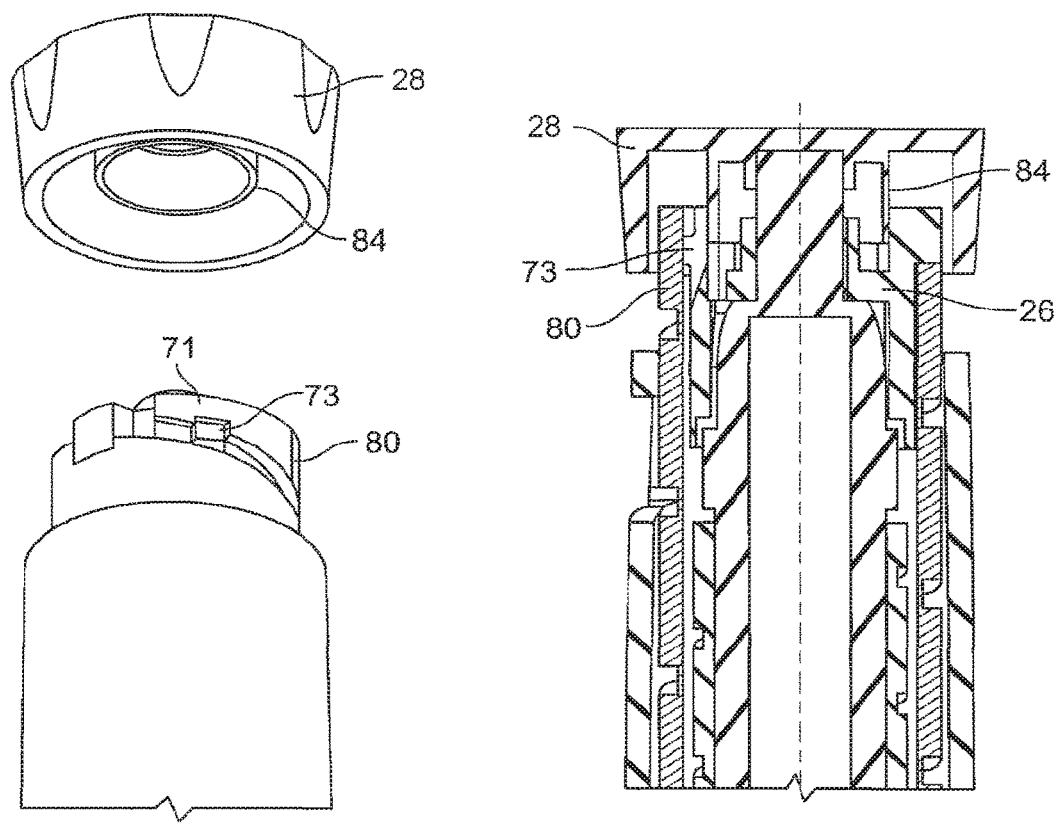
FIG. 10 is a perspective view and a cross-sectional view of a fifth embodiment of a drive assembly where an ring is incorporated as part of the dose knob such that when assembled it fits over the proximal end of the number sleeve to prevent movement of the clutch assembly fingers.

Yet another solution to prevent disassembling and ultimately counterfeiting of the device is presented in FIG. 10 where the dose knob 28 contains an inner ring 84 extending distally from an inside surface of the dose knob 28. When the dose knob 28 is connected to the dial link stem 42 during device assembly the ring 84 will be positioned on the inside of the assembly fingers 73. In a similar fashion as described above for the inner ring 82 or the ring segment, the dose knob ring 84 will also prevent the assembly fingers 73 from being flexed inwardly if a tool is placed in the cut-out through holes 71. If the assembly fingers 73 are prevented from flexing inward they will remain engaged with the cut-out through holes 71 and the clutch 26 will remain connected to the number sleeve 24 preventing the device from being disassembled by a counterfeiter. Instead of the dose knob ring 84—formed by one piece—at least one ring segment can be formed on the dose knob 28.

Disposed between the clutch 26 and the inside portion of the dose knob 28 is the compression or biasing spring 27 that urges the clutch 26 to engage the teeth 41 on the dial link 25. During injection, when a user manually applies a plunging force onto the proximal face of the dose knob 28, the spring 27 is elastically compressed, thus disengaging the clutch 26 and the number sleeve 24 from the dial link 25. Flange teeth 41 on the dial link 25 and clutch teeth 54 mesh when the spring 27 has biased the clutch 26 and attached the number sleeve 24 to the dose knob 28 and the dial link 25. The dose knob 28 and the dial link 25 are not meshed with the clutch 26 and the number sleeve 24 when the spring 27 has been sufficiently compressed during injecting. While a helically coiled metal wire spring is shown, other forms of commonly known biasing elements may be substituted.

The inner sleeve 29 is injection molded from plastic and includes a tubular body that fits into the hollow 65 of the number sleeve 24. The inner sleeve 29 has a helical threading 75 on its outer surface that engages the internal threading 67 on the inside surface of the number sleeve 24. Threadings 67 and 75 are shown as a single start threading, but may be differently formed. The proximal most portion of the end of inner sleeve 24, which end is partially helically shaped corresponding to the threading, is notched to form a partial ring of axially projecting teeth 76 that, when meshed with dial link distally facing teeth 39, serve to rotatably lock together the dial link 25 and the inner sleeve 29. The inner sleeve 29 is keyed to the pen body 4 through the intermediate mid-body 20 that is axially and rotatably fixed to the body 4. The distal end of the inner sleeve 29 has a pair of ridge-defined slots 77 on the periphery of the inner sleeve 29 which axially, slidably receive lugs 78 radially inwardly projecting from the mid-body 20. Openings molded into the inner sleeve 29 define four resilient fingers 38 having radially inwardly projecting teeth that are axially oriented and shaped to project into a recess in the distal end of the drive nut 23 that has radially projecting teeth or ridges 35 such that the inwardly projecting teeth click over, in either rotational direction, the teeth 35 during dose setting. The fingers 38 with teeth cooperate with the recess on the drive nut 23 to hinder the drive nut 23 from coming off the inner sleeve 29 after being assembled thereto during manufacture.

To facilitate back-driving during dose delivery, the threaded connections of the number sleeve 24 and the body 4, and the number sleeve 24 and the inner sleeve 29, are non-binding and provided by projecting 60° face angle threads that slide within correspondingly designed recessed grooves. With these threadings, it is preferred that the mechanical advantage is 3.4 or greater, and the screw lead of the drive member or drive nut 23 is 0.108 inch.

The operation of the above described embodiment will now be explained. The pen 1 with a needle 16 attached should first be primed to remove any trap air in the cartridge 8 and to ensure the bearing 21 is in contact with the proximal end of the cartridge stopper or piston 10. In particular, typically while clutching the pen body 4 in one hand, a user manually grips the dose knob skirt 50 and then begins to turn the knob 28 relative to the body 4. At the zero dose arrangement, and as long as the knob 28 is not also being plunged which is improper, the knob 28 can only be rotated in a dose increasing direction due to the number sleeve 24 not being further movable distally. A user stops the rotating after a short amount of travel of the number sleeve 24 that is associated with a small delivery volume, such as one or two units, which is indicated by markings visible through a window 51. Then, and after removing the cap 14 and any other needle cap present, and while pointing the needle tip upward, the user applies a plunging force on the dose knob 28 to drive it distally until the number sleeve 24 returns to the zero dose position, at which the number sleeve threading 52 has reached the distal end of the body threading 62, during which plunging action the piston 10 is shifted forward within the cartridge 8. If a user sees that the piston movement has caused liquid to reach the needle distal tip, the priming process is complete. If no liquid is visible at the needle tip, the priming steps are repeated as needed. After priming, the pen 1 is ready to be used for an actual injection.

First, a user prepares the pen by setting the desired dose, as visible in the window 51, by turning of the knob 28. If the user dials up too large of a dose, and without expelling any medicine, the user can rotate down the dial by turning the knob 28 in the opposite direction, all the way back to zero if desired. To set a dose, the knob 28 is turned in a clockwise direction. Because the dose knob 28 and the dial link 25 are fixed rotationally, the dial link 25 is rotated causing the distally facing fingers 43 to engage the proximally facing fingers 36 of the drive nut 23 to thereby turn the drive nut 23 in same direction. Rotation of the drive nut 23 causes the drive nut 23 to rotate relative to the stationary lead screw 22 whereby the drive nut 23 moves or climbs up the lead screw 22 in the proximal direction. The drive nut 23 rotates relative to the inner sleeve 29 that is held rotationally fixed relative to the body 4 through the splined connection to the mid-body 20. Because the drive nut 23 and the inner sleeve 29 are axially fixed, proximal axial movement of the drive nut 23 causes the inner sleeve 29 to slide proximally relative to the mid-body 20. Because the clutch 26 is rotationally fixed with the dial link 25, the clutch 26 rotates causing the number sleeve 24 to rotate and to spin out proximally away from body 4. Because the pitch of the threads on the number sleeve 24 are greater than the pitch of the threads on the inner sleeve 29, the number sleeve 24 and the dial link 25 will translate a larger axial distance as compared to the inner sleeve and the drive nut.

To inject the dose, after pen 1 is manipulated so the injection needle distal tip properly penetrates, for example, a user's skin, an axial, distal plunging force is applied to the knob face 53 to force the dial link 25 axially in the distal direction toward the body 4, such as with a thumb or index finger of the hand which grasps the housing 4. Initially during injecting, the dial link 25 is shifted axially, which shifting motion compresses the biasing spring 27 to close the gap between the knob surface and the proximal end of the number sleeve 24. The biasing spring 27 is designed to compress prior to the number sleeve 24 moving relative to the body 4. When the dial link 25 shifts relative to the number sleeve 24 to the axial arrangement of the drive nut 23, the clutch teeth 54 and dial link teeth 42 disengage to allow a backdriving rotation of the number sleeve 24 relative to the dial link 25. During the axial movement of the dial link 25, the drive nut 23 does not move axially or rotationally. When the number sleeve 24 and the clutch 26 rotatably uncouple from the dial link 25, as the dial link 25 is continued to be axially plunged without rotation by the user by the plunging of the knob 28, the number sleeve 24 screws into the body 4 as it spins relative to knob 28 and the dose markings on the number sleeve 24 that indicate the amount still remaining to be injected are visible through the window 51.

As it screws down, the number sleeve 24 causes the inner sleeve 29 to in essence screw up the internal thread inside of the number sleeve threading as the inner sleeve 29 advances distally a lesser distance than the number sleeve 24. The advancement of the inner sleeve 29, due to the abutting or direct engagement with the distal end of the drive nut 23, advances the drive nut 23 without rotation, which due to its threaded connection with the lead screw 22 advances the lead screw 22 axially without rotation, which lead screw advancement shifts the cartridge piston 10 to expel medication from the cartridge reservoir. The injection is completed when the number sleeve threading 52 has reached the distal end of the body 4, at which time pen 1 is once again arranged in the ready state or zero dose position.

Pen 1 can continue to be used to deliver any desired dose until the medicine remaining in the cartridge 8 is insufficient for a proper dosing. This insufficiency is indicated to the user by the inability to fully set the desired dose due to drive nut threading 37 abutting the thread stop 34 of the lead screw 22, at which time the drive nut 23 and the dial link 25 cannot be rotated proximally any farther. When insufficient medicine remains, the pen 1 is to be disposed of and replaced with a similar but entirely new pen.

The terms "medicament" or "medicinal product", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the aforementioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates

While this invention has been shown and described as having various designs, the present invention may be modified within the spirit and scope of this disclosure. For example, to deliver a fixed dose, the pen 1 would preferably be modified such that the maximum that the dial could be screwed out to prepare the pen 1 for injection would correspond to the fixed dose. Such a fixed dose pen could eliminate numerical dosage indicating marking, and instead provide user cues in the form of, for example, instructions and a graphical dosing indicator. This disclosure is therefore intended to cover any variations, uses or adaptations of the invention using its general principles. Further, this disclosure is intended to cover such departures from the present disclosure as come within known or customary practice in the art to which this invention pertains.

The invention claimed is:

1. A drive assembly for a drug delivery device, the drive assembly comprising:
   a housing;
   a number sleeve accommodated within the housing and having inner and outer proximal sections;
   a dial link rotatably fixed with the number sleeve when the dial link and the number sleeve are in a first axial arrangement relative to each other, the number sleeve being rotatable relative to the dial link when the dial link and the number sleeve are in a second axial arrangement; and
   a clutch component connected to the inner proximal section of the number sleeve through a plurality of flexible assembly fingers, wherein the clutch component is configured to engage the number sleeve with the dial link in the first axial arrangement of the dial link and the number sleeve and is configured to disengage the number sleeve from the dial link in the second axial arrangement of the dial link and the number sleeve, wherein the clutch component is configured to be disengaged from the dial link in the second axial arrangement of the dial link and the number sleeve, wherein the number sleeve and the clutch component are separate parts which are assembled to one another and retained together by the plurality of flexible assembly fingers, and wherein the drive assembly provides means for preventing
an access to the plurality of flexible assembly fingers from the outer proximal section of the number sleeve and/or
the plurality of flexible assembly fingers from flexing inwardly and disengaging from the connection with the inner proximal section of the number sleeve.

2. The drive assembly according to claim 1, comprising a dose knob connected to the dial link and provided for setting a predetermined dose of a medicament by a screwing motion of the dial link and the number sleeve relative to the housing in the first axial arrangement of the dial link and the number sleeve and provided for delivering the set dose of the medicament by a screwing motion of the number sleeve relative to the housing in the second axial arrangement of the dial link and the number sleeve,
wherein the dose knob is provided for axially moving the dial link relative to the number sleeve so as to switch the dial link and the number sleeve between the first and the second axial arrangement.

3. The drive assembly according to claim 2, wherein the plurality of flexible assembly fingers is engaged with cut-out through holes in the outer proximal section of the number sleeve and wherein the means for preventing the access to the plurality of flexible assembly fingers from the outer proximal section of the number sleeve are formed by wall segments of the dose knob covering the cut-out through holes in the outer proximal section of the number sleeve for blocking the access to the plurality of flexible assembly fingers.

4. The drive assembly according to claim 1, wherein the plurality of flexible assembly fingers is engaged with cut-out through holes in the outer proximal section of the number sleeve and wherein the means for preventing the access to the plurality of flexible assembly fingers from the outer proximal section of the number sleeve are formed by at least one ring which is positioned around the outer proximal section of the number sleeve so as to cover the cut-out through holes for blocking the access to the plurality of flexible assembly fingers.

5. The drive assembly according to claim 1, wherein the means for preventing the access to the plurality of flexible assembly fingers from the outer proximal section of the number sleeve are formed by wall segments of the outer proximal section of the number sleeve such that the plurality of flexible assembly fingers are in a snap fit engagement with detent pockets on the inner proximal section of the number sleeve at an opposite side of the wall segments of the outer proximal section of the number sleeve.

6. The drive assembly according to claim 1, wherein the means for preventing the plurality of flexible assembly fingers from flexing inwardly and disengaging from the connection with the inner proximal section of the number sleeve are formed by at least one ring or at least one ring segment which is positioned in an annular space between the dial link and the plurality of flexible assembly fingers so as to block the plurality of flexible assembly fingers from flexing inwardly.

7. The drive assembly according to claim 6, further comprising a dose knob connected to the dial link and provided for setting a predetermined dose of a medicament by a screwing motion of the dial link and number sleeve relative to the housing in the first axial arrangement of the dial link and the number sleeve and provided for delivering the set dose of the medicament by a screwing motion of the number sleeve relative to the housing in the second axial arrangement of the dial link and the number sleeve,
wherein the dose knob is provided for axially moving the dial link relative to the number sleeve so as to switch the dial link and the number sleeve between the first and the second axial arrangement, and
wherein the at least one ring or the at least one ring segment is an integral part of the dose knob.

8. The drive assembly according to claim 1, wherein the dial link and the number sleeve are in the first axial arrangement during a dose setting operation of the drive assembly and in the second axial arrangement during a dose delivery operation of the drive assembly.

9. A drug delivery device comprising a drive assembly according to claim 1, the drug delivery device further comprising:
a lead screw having a distal end and a proximal end and being rotatably fixed during dose setting and during dose delivery and axially movable in a distal direction relative to the housing, the lead screw including a threaded shaft and a bearing foot connected to the distal end; and
a drive nut threadedly engaged and screwable along the threaded shaft of the lead screw, wherein the dial link is connected with the drive nut and axially movable and rotatably fixed relative to the drive nut,
wherein during dose setting, the dial link and the number sleeve are in the first axial arrangement, whereby a screwing motion of the dial link and the number sleeve relative to the housing screws the dial link and the number sleeve a first axial distance from a home position, the screwing motion of the dial link screwing the drive nut along the threaded shaft of the lead screw a second axial distance that is different than the first axial distance, and
wherein during dose delivery, the dial link and the number sleeve are in the second axial arrangement, whereby a screwing motion of the number sleeve relative to the housing back toward the home position axially advances the drive nut and thereby the lead screw in the distal direction to dispense a predetermined dose of a medicament.

10. The drug delivery device according to claim 9, further comprising a cartridge with a movable piston at one end and an outlet at another end, the piston being engagable by the bearing foot of the lead screw to be advanced toward the outlet when the lead screw is moved distally so as to dispense fluid from the outlet of the cartridge.

11. The drug delivery device according to claim 10, further comprising an inner sleeve threadedly engaged with the number sleeve and axially movable and rotatably fixed relative to the housing, the drive nut being axially fixed to the inner sleeve,
wherein the screwing motion of the number sleeve relative to the housing back toward the home position advances the inner sleeve without rotation in the distal direction to axially advance the drive nut and thereby the lead screw and the movable piston to dispense fluid from the outlet of the cartridge.

12. The drug delivery device according to claim 11, wherein a threading of the number sleeve to the housing is of a first lead, a threading of the inner sleeve to the number sleeve is of a second lead, and a threading of the threaded shaft of the lead screw is of a third lead, whereby the first lead, the second lead and the third lead are different from each other.

13. The drug delivery device according to claim 11, further comprising a mid-body axially fixed inside of the housing, the mid-body including tabs that slidably fit within keyways in the lead screw to prevent rotation of the lead screw within housing,
wherein the inner sleeve is axially movable and rotatably fixed relative to the mid-body by at least one lug of the mid-body that slidably fits within at least one slot formed in the inner sleeve.

14. A drive assembly for a drug delivery device, the drive assembly comprising:
a housing;
a number sleeve accommodated within the housing and having inner and outer proximal sections;
a dial link rotatably fixed with the number sleeve when the dial link and the number sleeve are in a first axial arrangement relative to each other, the number sleeve being rotatable relative to the dial link when the dial link and the number sleeve are in a second axial arrangement;
a clutch component connected to the inner proximal section of the number sleeve through a plurality of flexible assembly fingers, the clutch component being configured to engage the number sleeve with the dial link in the first axial arrangement of the dial link and the number sleeve and to disengage the number sleeve from the dial link in the second axial arrangement of the dial link and the number sleeve; and
a dose knob connected to the dial link and provided for setting a predetermined dose of a medicament by a screwing motion of the dial link and the number sleeve relative to the housing in the first axial arrangement of the dial link and the number sleeve and provided for delivering the set dose of the medicament by a screwing motion of the number sleeve relative to the housing in the second axial arrangement of the dial link and number sleeve, the dose knob being provided for axially moving the dial link relative to the number sleeve so as to switch the dial link and the number sleeve between the first and the second axial arrangement,
wherein the number sleeve and the clutch component are separate parts which are assembled to one another and retained together by the plurality of flexible assembly fingers, and
wherein the drive assembly provides means for preventing
an access to the plurality of flexible assembly fingers from the outer proximal section of the number sleeve and/or
the plurality of flexible assembly fingers from flexing inwardly and disengaging from the connection with the inner proximal section of the number sleeve.

15. A drive assembly for a drug delivery device, the drive assembly comprising:
a housing;
a number sleeve accommodated within the housing and having inner and outer proximal sections;
a dial link rotatably fixed with the number sleeve when the dial link and the number sleeve are in a first axial arrangement relative to each other, the number sleeve being rotatable relative to the dial link when the dial link and the number sleeve are in a second axial arrangement; and
a clutch component connected to the inner proximal section of the number sleeve through a plurality of flexible assembly fingers, the clutch component being configured to engage the number sleeve with the dial link in the first axial arrangement of the dial link and the number sleeve and to disengage the number sleeve from the dial link in the second axial arrangement of the dial link and the number sleeve,
wherein the number sleeve and the clutch component are separate parts which are assembled to one another and retained together by the plurality of flexible assembly fingers,
wherein the drive assembly provides means for preventing
an access to the plurality of flexible assembly fingers from the outer proximal section of the number sleeve and/or
the plurality of flexible assembly fingers from flexing inwardly and disengaging from the connection with the inner proximal section of the number sleeve, and
wherein the plurality of flexible assembly fingers is engaged with cut-out through holes in the outer proximal section of the number sleeve and wherein the means for preventing the access to the plurality of flexible assembly fingers from the outer proximal section of the number sleeve are formed by at least one ring which is positioned around the outer proximal section of the number sleeve so as to cover the cut-out through holes for blocking the access to the plurality of flexible assembly fingers.

16. A drug delivery device comprising:
a drive assembly comprising
a housing,
a number sleeve accommodated within the housing and having inner and outer proximal sections,
a dial link rotatably fixed with the number sleeve when the dial link and the number sleeve are in a first axial arrangement relative to each other, the number sleeve being rotatable relative to the dial link when the dial link and the number sleeve are in a second axial arrangement, and
a clutch component connected to the inner proximal section of the number sleeve through a plurality of flexible assembly fingers, the clutch component being configured to engage the number sleeve with the dial link in the first axial arrangement of the dial link and the number sleeve and to disengage the number sleeve from the dial link in the second axial arrangement of the dial link and the number sleeve;
a lead screw having a distal end and a proximal end and being rotatably fixed during dose setting and during dose delivery and axially movable in a distal direction relative to the housing, the lead screw including a threaded shaft and a bearing foot connected to the distal end; and
a drive nut threadedly engaged and screwable along the threaded shaft of the lead screw, wherein the dial link is connected with the drive nut and axially movable and rotatably fixed relative to the drive nut, wherein the number sleeve and the clutch component are separate parts which are assembled to one another and retained together by the plurality of flexible assembly fingers, wherein the drive assembly provides means for preventing an access to the plurality of flexible assembly fingers from the outer proximal section of the number sleeve and/or the plurality of flexible assembly fingers from flexing inwardly and disengaging from the connection with the inner proximal section of the number sleeve, wherein during dose setting, the dial link and the number sleeve are in the first axial arrangement, whereby a screwing motion of the dial link and the number sleeve relative to the housing screws the dial link and the number sleeve a first axial distance from a home position, the screwing motion of the dial link screwing the drive nut along the threaded shaft of the lead screw a second axial distance that is different than the first axial distance, and wherein during dose delivery, the dial link and the number sleeve are in the second axial arrangement, whereby a screwing motion of the number sleeve relative to the housing back toward the home position axially advances the drive nut and thereby the lead screw in the distal direction to dispense a predetermined dose of a medicament.

* * * * *

UNITED STATES PATENT AND TRADEMARK OFFICE
CERTIFICATE OF CORRECTION

PATENT NO. : 10,314,982 B2
APPLICATION NO. : 15/031723
DATED : June 11, 2019
INVENTOR(S) : Stefan Blancke et al.

Page 1 of 1

It is certified that error appears in the above-identified patent and that said Letters Patent is hereby corrected as shown below:

In the Specification

Column 1, Line 11, after "filed", insert -- on November 22, 2013, and Application No. EP14165744.5, filed on --.

Signed and Sealed this
Twenty-sixth Day of November, 2019

Andrei Iancu
*Director of the United States Patent and Trademark Office*

UNITED STATES PATENT AND TRADEMARK OFFICE
CERTIFICATE OF CORRECTION

PATENT NO. : 10,314,982 B2
APPLICATION NO. : 15/031723
DATED : June 11, 2019
INVENTOR(S) : Stefan Blancke Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 276 days.

Signed and Sealed this
Twenty-sixth Day of May, 2020

Andrei Iancu
*Director of the United States Patent and Trademark Office*